United States Patent [19]

Hjerten

[11] Patent Number: 4,680,201
[45] Date of Patent: Jul. 14, 1987

[54] COATING FOR ELECTROPHORESIS TUBE

[76] Inventor: Stellan Hjerten, Institute of Biochemistry, University of Uppsala Biomedical Center, P.O. Box 576, S-751 23, Uppsala, Sweden

[21] Appl. No.: 792,724

[22] Filed: Oct. 30, 1985

[51] Int. Cl.$^4$ .............................................. B05D 7/22
[52] U.S. Cl. .................... 427/230; 65/30.1; 65/3.41; 427/239; 427/302; 204/182.9
[58] Field of Search ............ 427/239, 230, 387, 389.7, 427/302; 65/30.1, 3.41

[56] References Cited

U.S. PATENT DOCUMENTS

| | | | |
|---|---|---|---|
| 3,276,853 | 10/1966 | Eakins | 65/3.41 |
| 4,372,850 | 2/1983 | Okumura et al. | 427/389.7 X |
| 4,376,641 | 3/1983 | Nestrick et al. | 65/30.1 |
| 4,409,266 | 10/1983 | Wieczorrer et al. | 427/302 |
| 4,509,964 | 4/1985 | Hubball et al. | 55/386 |
| 4,548,842 | 10/1985 | Pohl | 427/389.7 X |
| 4,567,107 | 1/1986 | Rizk et al. | 427/389.7 X |
| 4,589,964 | 5/1986 | Mayhan et al. | 427/302 X |

*Primary Examiner*—Thurman K. Page
*Attorney, Agent, or Firm*—Townsend & Townsend

[57] ABSTRACT

Coated capillary tubes useful for performing free electrophoretic separation techniques are prepared by reacting the interior wall of the tube with a bifunctional compound having a first functional group capable of covalently attaching to the wall and a second functional group capable of being polymerized. After such covalent attachment, free monomer is reacted with the second functional group, resulting in the formation of a monomolecular polymeric layer covalently attached to the interior wall of the capillary tube. This polymeric layer inhibits electroendosmosis and adsorption of the substances to be separated onto the interior of the tube, providing for improved separation.

6 Claims, 5 Drawing Figures

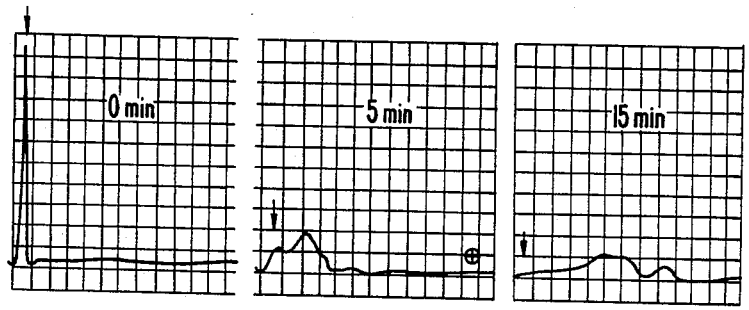
FIG._1A.
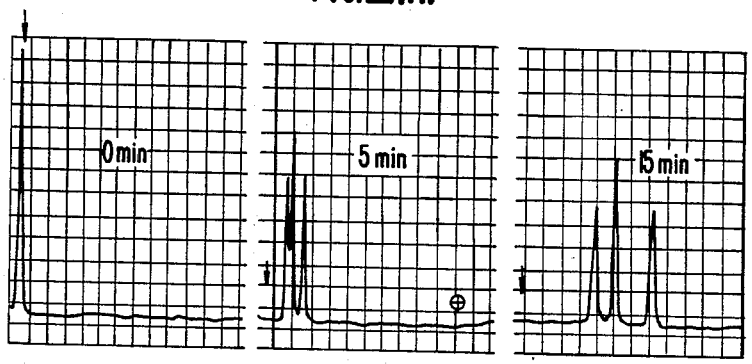
FIG._1B.
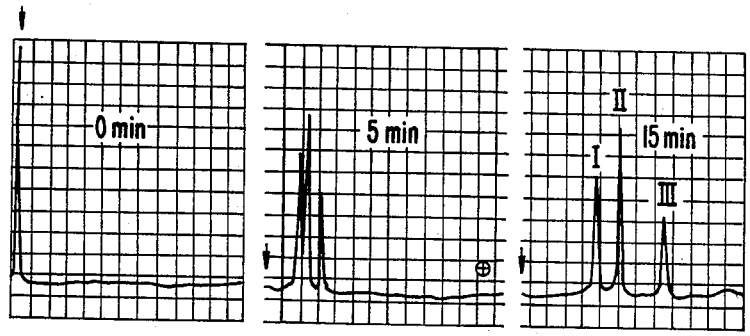
FIG._1C.

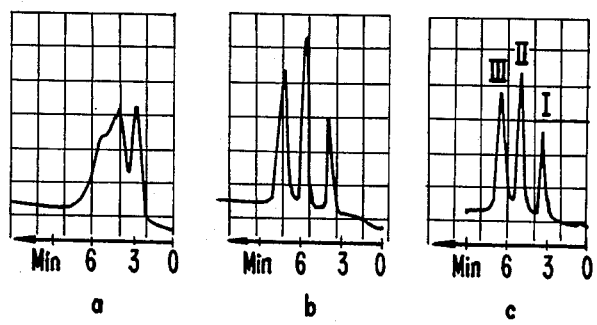
FIG._2.
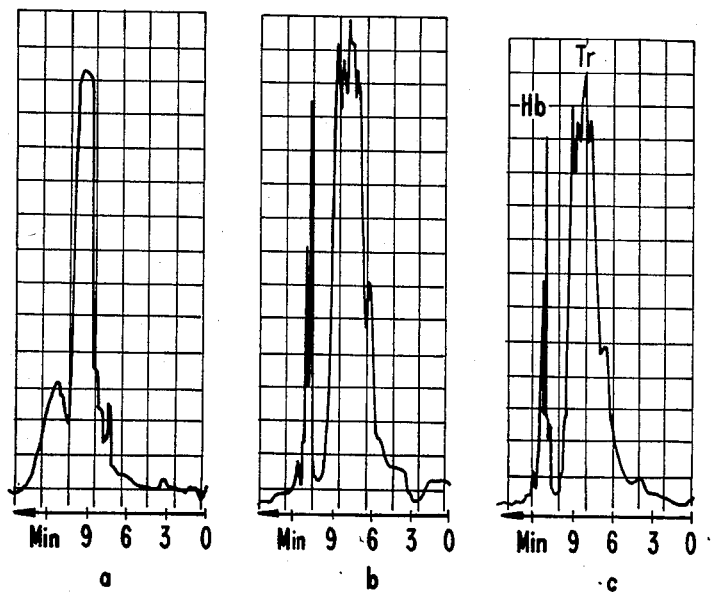
FIG._3.

COATING FOR ELECTROPHORESIS TUBE

BACKGROUND OF THE INVENTION

1. Field of the Invention

The present invention relates generally to apparatus for performing electrophoresis, and in particular to improved materials and methods for coating electrophoresis tubes to inhibit zone distortion resulting from electroendoosmosis and adsorption of solutes on the inner surface of the tube.

2. Description of the Background Art

Electrophoretic separation techniques, including zone electrophoresis, displacement electrophoresis (isotachophoresis), and isoelectric focusing may be performed in a variety of apparatus. Of interest to the present invention is the use of thin-walled, narrow-bore capillary tubes for containing the carrier-free separation medium. Such tubes are particularly useful since zone deformation caused by the evolution of heat during the electrophoretic separation is negligible.

The use of capillary tubes in electrophoresis techniques, however, results in zone deformation arising from other mechanisms, including both electroendosmosis and adsorption of the substances to be separated resulting, for example, from interaction of the substance with charges on the inner tube surface. Zone deformation is a particular problem with macromolecular substances, such as proteins, which possess multiple binding sites capable of interacting strongly with the inner wall of the tube. The problem is acute in zone electrophoresis where the zones are not as well defined as with other techniques, such as isoelectric focusing, where the zones are substantially sharpened.

The problems associated with adsorption and electroendoosmosis have been largely overcome by coating the inner wall of the electrophoresis tube with various polymeric substances. One of the most successful techniques has been the use of methylcellulose as described by Hjertén (1967) Chromatogr. Rev. 9:122–219. The methylcellulose is applied by baking at an elevated temperature and low pH in the presence of formaldehyde. Although successful, the method suffers from a number of drawbacks. The methylcellulose is adsorbed to the glass (quartz) surface and must therefore be renewed after about five days. Moreover, the thickness of the coating is non-uniform so that a relatively thick application is required to assure that the entire area is sufficiently covered. Also, it is difficult to work with the methylcellulose since it is highly viscous. For instance, due to the high viscosity, it is virtually impossible to fill a capillary electrophoresis tube with an inner diameter as small as 0.05 mm with the methylcellulose solution, which is one step in the coating procedure. Finally, in both the methylcellulose coated tubes and in the tubes coated as described herein the viscosity is higher at the wall than at the axis of the tube—a condition that eliminates electroendosmosis as shown by Hjertén, supra. This difference in viscosity causes the solutes to migrate more slowly at the wall than at the axis of the tube which is equivalent to a zone deformation. However, since the tubes coated as described herein have a very thin monomolecular coating the zone deformation is negligible, while the methylcellulose-coated tubes have a much thicker coating and therefore may cause an observable zone deformation, particularly when the tubes are very narrow since the coating then will represent percentually a large part of the tube volume.

Other coating materials have also been proposed for electrophoretic applications. Jorgensen et al. (1983) Science 222:266–272, describe the use of silica tubes modified with glycol groups to decrease the adsorption of proteins. The reported results clearly indicate that electroendoosmosis in such tubes is still very pronounced and therefore also the adsorption. Radola (1980) Electrophoresis 1:43–56, describes isoelectric focusing using gels of cross-linked polyacrylamide covalently bound to glass plates or polyester films pretreated with γ-methacryloxypropyltrimethoxysilane. The purpose of this pretreatment is only to fix the gel to the glass or the polyester. In that technique the gel fills the whole separation chamber. The separations are accordingly not performed in free solution as is the case with the present invention and therefore no problems with electroendosmosis occur.

SUMMARY OF THE INVENTION

The present invention provides improved coated capillary tubes for use in free electrophoretic separation techniques, including zone electrophoresis, displacement electrophoresis, and isoelectric focusing. The coating is a monomolecular polymer layer polymerized in situ on the inner wall of the capillary tube. A bifunctional compound having one functional group capable of being covalently attached to the tube wall and a second functional group capable of being polymerized is attached to the wall through the first functional group. The second functional group is then reacted with free monomer under conditions selected to form the monomolecular polymeric layer. In the exemplary embodiment, γ-methacryloxypropyltrimethoxysilane is attached to a glass tube through the methoxy group, and the acryl group is reacted with a free acryl monomer, such as acrylamide. No cross linking agent is used as is the case in the preparation of gels.

By polymerizing the coating layer in situ, it is possible to employ low viscosity compounds in the method, while obtaining a high viscosity coating which is very effective in inhibiting electroendosmosis and solute interaction with the tube wall. Moreover, the resulting layer is covalently attached to the wall and is monomolecular and yet covers the entire area of the inner wall. This is in great contrast to the methylcellulose method described above which results in an excessively thick layer adsorbed onto the tube wall.

BRIEF DESCRIPTION OF THE DRAWINGS

FIGS. 1A–1C illustrate the relative quality of zone electrophoresis obtained with an uncoated tube (FIG. 1A), a tube coated with a monomolecular polyacrylamide layer (FIG. 1B), and a methylcellulose coated tube (FIG. 1C).

FIG. 2 illustrates the relative quality of high performance electrophoresis obtained with an uncoated tube (a), a polyacrylamide coated tube (b), and a methylcellulose coated tube (c).

FIG. 3 illustrates a comparison of isoelectric focusing using an uncoated tube (a), a polyacrylamide coated tube (b), and a methylcellulose coated tube (c).

DESCRIPTION OF THE SPECIFIC EMBODIMENTS

The present invention utilizes conventional glass or quartz capillary tubes or plastic tubes where the plastic contains free hydroxyl (OH) groups. The dimensions of the tube are not critical, but will usually have an inner diameter from about 0.02 to 0.8 mm and a length in the range from about 50 to 1000 mm, more usually in the range from about 100 to 200 mm.

The inner walls of the capillary tube are coated with a monomolecular polymeric layer in order to inhibit electroendosmosis and interaction between the tube wall and with the substances to be electrophoretically separated. The coating procedure employs a bifunctional compound having a first functional group, such as a methoxy, acetoxy, methoxyethoxy, or chloro, capable of acting with the free hydroxyl groups in the tube wall, and a second functional group, such as an acryl, acryloyl, methacryl, allyl or vinyl, capable of being polymerized. Suitable bifunctional compounds include γ-methacryloxypropyltrimethoxysilane, vinyltriacetoxysilane, vinyltri(β-methoxyethoxy)silane, vinyltrichlorosilane, and methylvinyldichlorosilane, particularly γ-methacryloxypropyltrimethoxysilane. After the bifunctional compound is reacted with the tube wall under conditions which result in covalent attachment through the first functional group, the second functional group is reacted with free monomer, such as acrylamide acryloylmorpholine, ethylene glycol methacrylate, or vinyl alcohol, to form the polymeric layer. Illustrative polymeric layers include non-crosslinked polyacrylamide, polyacryloylmorpholine, poly(ethylene glycol methacrylate), polyvinyl pyrrolidone, polyvinyl alcohol, and the like. The non-covalently attached polymer is then removed simply by rinsing with water, resulting in a thin, well-defined monomolecular layer of the polymer covalently bound to the tube wall.

After drying, typically in an oven at a elevated temperature (35° to 120° C.), the coated capillary tubes are ready for use as electrophoresis tubes in the well known manner.

The following experimental results are offered by way of illustration, not by way of limitation.

EXPERIMENTAL

Materials and Methods

γ-Methacryloxypropyltrimethoxysilane was obtained from Pharmacia Fine Chemicals AB, Sweden. Carrier ampholytes for isoelectric focusing (Pharmalyte TM) were also a Pharmacia product. Acrylamide, potassium persulfate and N,N,N',N'-tetramethylethylenediamine (TEMED) were of electrophoresis grade and purchased from Bio-Rad Laboratories, Richmond, Calif. Terephthalic acid, 4-hydroxybenzoic acid and β-naphthylacetic acid were kindly supplied by Dr. K. G. Wahlund, Department of Analytical Pharmaceutical Chemistry, BMC, Uppsala, Sweden. Human transferrin was a gift from KABI/VITRUM, Stockholm, Sweden. Human hemoglobin was prepared from outdated blood delivered by the Academic Hospital, Uppsala, Sweden.

Electrophoresis tubes were prepared by covalently bonding γ-methacryloxypropyltrimethoxysilane to the inner wall of a glass capillary tube as follows. About 80 μl of γ-methacryloxypropyltrimethoxysilane was mixed with 20 ml of water, the pH of which had been adjusted to 3.5 by acetic acid, and the resulting solution sucked up into the glass capillary tubes. After reaction at room temperature for one hour, the silane solution was expelled. The tubes were then washed with water and filled with a deaerated 3 or 4% (w/v) acrylamide solution containing 1 μl TEMED and 1 mg potassium persulfate per ml solution. After half an hour, the excess (not attached) polyacrylamide was sucked away, and the tubes were rinsed with water. Most of the water in the tubes was aspirated off, and the remainder was removed by drying in an oven at 35° C. for 45 minutes.

RESULTS

1. Zone electrophoresis in coated and non-coated tubes

The first experiments were performed with a free zone electrophoresis apparatus where convective disturbances are eliminated by rotating a horizontal quartz electrophoresis tube of length 380 mm and inner diameter 3 mm, as described by Hjertén (1967) Chromatogr. Rev. 9:122–219. The sample consisted of an artificial mixture of aromatic carboxylic acids (terephthalic acid, 4-hydroxybenzoic acid, and β-naphtylacetic acid). The runs were carried out in a 0.1 M Tris-acetic acid buffer (pH 8.6) at 1,840 volts (2.6 mA). The rotating tube was scanned with light of the wavelengths 280 and 310 nm at the start and after electrophoresis for 5 and 15 min. The ratio between the transmissions at these wavelengths was automatically recorded to suppress noise and irregular variations in the base-line of the electropherogram, as described by Hjertén (1967), supra. The experiments were performed in a non-coated tube, the γ-methacryloxypropyltrimethoxysilane tube, and a methylcellulose-coated tube, where the methylcellulose coating was applied as described in Hjertén (1967), supra.

The peaks obtained from the uncoated tube displayed a very substantial zone broadening (FIG. 1A), while the peaks obtained from both the γ-methacryloxypropyltrimethoxysilane tube (FIG. 1B) and methylcellulose tube (FIG. 1C) were well defined with each having a substantially identical pattern.

The above experiments were then repeated with the difference that they were carried out in the high-performance electrophoresis apparatus, as described by Hjertén (1983) J. Chromatogr. 270:1–6. The electrophoresis tube had dimensions of 0.2 (i.d.)×0.4 (o.d.)×160 mm. The voltage applied was 2,000 volts (50 μA). The recording was done by on-tube absorption measurements at 280 nm, as described by Hjertén (1983), supra.

The results again demonstrated that use of the uncoated tube resulted in broadest peaks, with the two slowest migrating peaks substantially overlapping while both the γ-methacryloxypropyltrimethoxysilane-coated tube and the methylcelluose-coated tube provided three well-defined peaks which were substantially identical in each case (FIG. 2).

2. Isoelectric focusing in coated and non-coated tubes

The runs were performed in glass tubes (0.2 (i.d.)×0.4 (o.d.)×120 mm) filled with a mixture of human hemoglobin (final concentration: 3 μg/μl), human transferrin (final concentration: 5 μg/μl), and Pharmalyte TM, pH 3–10 (final concentration: 1%, v/v). The tube was coated with γ-methacryloxypropyltrimethoxysilane, as described above. The focusing was carried out in the high-performance electrophoresis apparatus (Hjertén (1983) supra.) with on-tube detection at 280 nm at 2,000 volts for about 15 min. with 0.02 M phosphoric acid as anolyte and 0.02 M sodium hydroxide as catholyte. Elution of the focused protein zones was achieved by replacing the anolyte with 0.02 M sodium hydroxide. The experiment was repeated in with a non-coated glass tube and a methylcellulose-coated tube.

As with the previous experiments, the peaks detected from the non-coated tube were broadened and indistinct, while the peaks from both the γ-methacryloxypropyltrimethoxysilane-coated tube and the methylcellulose-coated tube were distinct and substantially similar in pattern (FIG. 3).

These results demonstrate that coating of the interior of a narrow-bore electrophoresis tube with the polyacrylamides of the present invention provides for inhibition of zone deformation (zone broadening), including that due to both adsorption and electroendoosmosis, to an extent equal to that achieved by methylcellulose-coated tubes. The use of polyacrylamide-coated tubes is a great advantage since they are easier to prepare when the diameter of the tube is small. In addition, the coating is covalently linked to the tube wall, which gives a relatively strong bond. Furthermore, the viscosity is the same throughout the electrophoresis medium except in the coating, which, however, is monomolecular and therefore very thin which means that zone deformations caused by viscosity differences in the medium can be neglected.

Although the foregoing invention has been described in some detail by way of illustration and example for purposes of clarity of understanding, it will be obvious that certain changes and modifications may be practiced within the scope of the appended claims.

What is claimed is:

1. A method for preparing a thin-wall, narrow-bore capillary tube for use in electrophoretic separation, said method comprising:
    contacting a solution of a monomeric bifunctional compound with the inside of the tube, where the bifunctional compound includes a first functional group capable of covalent attachment to the tube wall and a second functional group capable of polymerization to form a monomolecular coating;
    washing the tube free of non-bound monomeric bifunctional compound; and
    introducing free monomer to the inside of the tube in order to react the covalently bound monomeric second functional group with free monomer to form a monomolecular polymeric coating.

2. A method as in claim 1, wherein the bifunctional compound is selected from the group consisting of γ-methacryloxypropyltrimethoxysilane, vinyltriacetoxysilane, vinyltri(β-methoxyethoxy)silane, vinyltrichlorosilane, and methylvinyldichlorosilane.

3. A method as in claim 2, wherein the free monomer is selected from the group consisting of acryl, acryloyl, methacryl, allyl, and vinyl monomers.

4. A method as in claim 1, wherein the tube is complsed of glass, quartz, or plastic.

5. A thin-wall, narrow-bore capillary tube prepared according to the method of claim 1.

6. A method for preparing a thin-wall, narrow-bore capillary tube for use in electrophoresis separation, said method comprising:
    contacting the inside wall of the tube with an aqueous solution of γ-methacryloxypropyltrimethoxysilane (MPTS) at a pH below about 4.0;
    washing the wall substantially free from non-bound MPTS; and
    contacting the inside wall of the tube with an aqueous acrylamide solution capable of reacting with the MPTS to form a covalently bound monomolecular polyacrylamide layer on the inside wall of the tube.

* * * * *